United States Patent [19]
Allegrini et al.

[11] Patent Number: 6,147,257
[45] Date of Patent: Nov. 14, 2000

[54] PROCESS FOR THE PREPARATION OF S-ALKYLCYSTEINES

[75] Inventors: Pietro Allegrini, Lonigo; Giuseppe Barreca, Caldiero; Elena Rossi, Cologna Veneta, all of Italy

[73] Assignee: Zambon Group S.p.A., Milan, Italy

[21] Appl. No.: 09/243,535

[22] Filed: Feb. 3, 1999

[30] Foreign Application Priority Data

Feb. 4, 1998 [IT] Italy .................................. MI98A0200

[51] Int. Cl.[7] ................................................. C07C 321/04
[52] U.S. Cl. ............................................................ 562/557
[58] Field of Search ............................................. 562/557

[56] References Cited

U.S. PATENT DOCUMENTS 5,644,028  7/1997  Mimoto et al. .

OTHER PUBLICATIONS

Vincent du Vincent, "The Oxidation of the Sulfur of Homocystine, Methionine, and S–Methylcysteine in the Animal Body" *Dept. of Biochemistry, George Washington University*, 1934, pp. 481–488.

Dah–Ren Hwang et al., "Total Synthesis of (+)–Sparsomycin. Approaches Using Cysteine and Serine Inversion [1]," *American Chemical Society* 1985, pp. 1254–1271.

Marvin D. Armstrong, "Thioether Derivatives of Cysteine and Homocystein," *University of Utah College of Medicine*, pp. 749–753.

Max Frankel et al., "Synthesis of Poly–S–Alkyl–L–cysteines". pp. 1390–1393.

Kiyoshi Yamauchi, "Milellar Methylating Agents:"Long–chain–alkyl dimethyl Sulphonium Iodides, *J. Chemical Society*, pp. 1941–1942.

Kiyoshi Yamauchi, "Action of Trimethyl Phosphate on Amino Acids. Selective Methylatin of 1–Ceysteine and Related Compounds", *Pergamon Press.*, 1977, No. 13, pp. 1199–1202.

Chemical Abstracts 6834 : 1955.
Chemical Abstracts 6834 : 1955.
Chemical Abstracts 85 : 99178d, 1976.
Chemical Abstracts. 124 176949j 1996.
Chemical Abstracts. 123 : 11549x 1996.
Chemical Abstracts 126 : 334437p 1997.
Chemical Abstracts 106: 169054p 1987.

H. D. Brown et al., "The antituberculous activity of some ethylmercapto compounds". *J. Amer. Chem. Compounds". J. Amer. Chem. Soc.*vol. 76, 1954, p 3860.

Database CAPLUS on STN, Acc. No. 1987:49338, Lissel et al., 'Use of dimethyul carbonate as a methylating agent under phase treansfer–catalyzed conditions.'Synthesis (1986), pp382–383 (abstract).

Database CAPLUS on STN, Acc. No. 1992:407569, SELVA ET AL., 'Esters and ortho esters as lkylating agents at high temperature. Applications to continuous–flow processes'.J. Chem. Soc., Perkin Trans. 2 (1992), (4), pp519–522 (abstract).

*Primary Examiner*—Paul J. Killos
*Assistant Examiner*—Brian J. Davis
*Attorney, Agent, or Firm*—Nikaido Marmelstein Murray & Oram, LLP

[57] ABSTRACT

A process for the preparation of S-alkylcysteines of formula

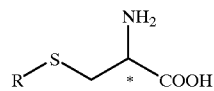

wherein R is a lower or branched $C_1$–$C_4$ alkyl group; by S-alkylation of cysteines with dialkylcarbonates.

13 Claims, No Drawings

PROCESS FOR THE PREPARATION OF S-ALKYLCYSTEINES

FIELD OF THE INVENTION

The present invention relates to a process for the preparation of S-alkylcysteines and, more particularly, it relates to a process for the preparation of S-alkylcysteines by alkylating the mercapto group of cysteines.

BACKGROUND OF THE INVENTION

S-alkylcysteines are known compounds, widely described in the literature.

For example, S-methylcysteines are claimed in WO 97/14430 (Pharmacia & Upjohn) as antioxidants for peptides and proteins, or they are used in the treatment of hepatic pathologies [*Chemical Abstracts* 106:169054p (1987)] or they are also used as oral antiseborrheic agents in U.S. Pat. No. 3,950,542 (Oreal S. A.).

Brown et al. describe S-ethylcysteines as antitubercolar agents [*J. Am. Chem. Soc.,* 76, 3860 (1954)].

Moreover, S-alkylcysteines can be used as synthetic intermediates for the preparation of compounds with pharmacological activity.

In particular, S-methylcysteines are used, for example, in the synthesis of antihypertensive agents (EP 266950—Pfizer; EP 254032—Schering), of antiviral agents (U.S. Pat. No. 5,644,028—Japan Energy Corporation), of antithrombotic agents (WO 95/28420—Corvas International, Inc.) or of metalloprotease inhibitors (WO 96/11209—Chiroscience Limited).

Several processes for the preparation of S-alkylcysteines are described in the literature.

In these context, the alkylation processes of the mercapto group of cysteines are of particular interest.

For example, D. H. Hwang et al. [*J. Org. Chem.,* 50, 1264 (1985)] describe the preparation of S-methyl-L-cysteine by methylating L-cysteine hydrochloride with methyl iodide and sodium ethoxide, the latter being formed in situ from metallic sodium and ethanol, in alcoholic medium.

M. Frankel et al. [*J. Chem. Soc.,* 1390 (1960)] report a process for the S-methylation of L-cysteine by Schotten-Baumann reaction in hydroalcoholic medium and in the presence of sodium hydroxide as a base and of methyl iodide as methylating agent.

According to a further version, described by H. Zahan et al. (*Chemical Abstracts* 49 6834e) the methylation reaction is carried out with methyl iodide and sodium bicarbonate in ethanol.

However, the use of methyl iodide shows not to be the best for the application on a large scale, because of its high toxicity and cost and because of the formation of elementary iodine which is difficult to dispose in the waste waters deriving from the work-up.

According to a similar synthetic process described by M. D. Amstrong et al. [*J. Org Chem.,* 16, 749 (1951)], S-ethyl-L-cysteine is prepared by S-ethylating with ethyl bromide the L-cysteine obtained in situ from L-cystine by reduction with metallic sodium and liquid ammonia. It is evident that, from an industrial viewpoint, this process results to be still more disadvantageous with respect to the previous ones because, in addition to the use of a toxic alkylating agent, it requires particular procedures and equipment for the storage and use of liquid ammonia under safety conditions.

Further processes described in the literature use different methylating agents.

For example, the use of dimethylsulfate in the presence of barium hydroxide is described by V. du Vigneaud et al. [*J. Biol. Chem.,* 105, 481 (1934)], but also dimethylsulfate is characterised by a high toxicity. The use of trimethylphosphate in aqueous solution at pH=8 is described by K. Yamauchi [*Tet. Lett.,* 1199 (1977)], but this alkylating agent is toxic by inhalation, skin contact or ingestion. Furthermore this synthesis results in a partial racemization (7.5%) of the substrate.

Most of the processes described in the literature for the synthesis of S-alkylcysteines uses an amount of alkylating agent higher than the stoichiometric one to bring to completion the alkylation reaction within an acceptable time period without using too much strong reaction conditions.

A drawback common to the above processes is the formation of significant amounts of salts, for example iodides or sulfates, deriving from the reaction itself but also from the decomposition process of the exceeding alkylating agent, during the final work-up.

Consequently, the isolation of very soluble S-alkylcysteines, such as S-methylcysteine, from an aqueous medium is particularly cumbersome so resulting in some cases in unsatisfactory yields.

Less common methylating agents, which can be used for the preparation of S-methylcysteines by S-methylation of cysteines, are the sulphonium salts of formula $RMe_2SI$, described by K. Yamauchi [*J. Chem. Soc. Perkin Trans. I,* 1941 (1983)]. However such alkylating agents, which can be easy removed by simple thermal decomposition and extraction with chlorinated solvents, are of no practical interest because they are not commercially available.

Therefore, the high toxicity or harmfulness of the alkylating agents, their high costs, the inevitable formation of remarkable amounts of salts in the reaction medium, so making complicate the process for the isolation of the final water-soluble product, and of waste waters difficult to dispose, the partial racemization of the substrate and, finally, the poor commercial availability of some reagents make the processes for the preparation of S-alkylcysteines described in the literature of difficult industrial applicability.

As far as we know, a process for the preparation of S-alkylcysteines by S-alkylation reaction with dialkylcarbonates has never been described in the literature.

SUMMARY OF THE INVENTION

We have now found a process for the preparation of S-alkylcysteines by S-alkylation of cysteines, under non-racemizing conditions, with harmless, easy available and inexpensive reagents which is particularly suitable for the industrial application.

Therefore, object of the present invention is a process for the preparation of S-alkylcysteines of formula

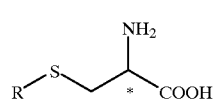

(I)

wherein

R is a linear or branched $C_1$–$C_4$ alkyl group;

the carbon atom marked by the asterisk is a stereogenic centre;

comprising the treatment of a compound of formula

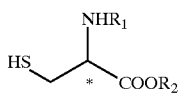
(II)

wherein
- $R_1$ is hydrogen or a linear or branched $C_1$–$C_6$ aliphatic acyl group, or an arylcarbonyl group, or an alkoxycarbonyl or aryloxycarbonyl group, wherein the alkyl moiety is an optionally substituted linear or branched $C_1$–$C_4$ alkyl;
- $R_2$ is a hydrogen atom or an optionally substituted linear or branched $C_1$–$C_6$ alkyl or an optionally substituted benzyl group;
- wherein the carbon atom marked by the asterisk has the above reported meaning;
- with a dialkylcarbonate of formula $$(RO)_2CO \quad (III)$$

wherein R has the above reported meanings;
- in the presence of a suitable organic or inorganic base;
- and the optional hydrolysis reaction, when one or both $R_1$ and $R_2$ are different from hydrogen.

The process object of the present invention can be easy carried out and allows to obtain the S-alkylcysteines of formula I in good yields with respect to the starting compound of formula II, without using toxic reagents.

The alkylation reaction according to the process object of the present invention is carried out by reacting a compound of formula II with a dialkylcarbonate of formula III.

The starting compounds of formula II are known compounds, commercially available or easy to prepare, for example according to the procedure described by M. D. Amstrong et al. [*J. Org. Chem.*, 16, 749 (1951)].

The starting compounds of formula II, when $R_1$ and $R_2$ are different from hydrogen, can be prepared from the corresponding cysteines, through the protection of the amino and carboxylic groups, according to conventional techniques.

In the compounds of formula II, $R_1$ and $R_2$ can be protective groups of the amino and of the carboxy functions selected among those more commonly used by the man skilled in the art, provided that they are compatible with the reaction conditions used in the process object of the present invention.

Preferred protective groups of the carboxy function are esters of optionally substituted linear or branched $C_1$–$C_6$ alcohols, for example methyl, ethyl, n-propyl, isopropyl, n-butyl, sec-butyl, isobutyl, tert-butyl, isopentyl, tert-pentyl, neo-pentyl, cyclopentyl, hexyl, cyclohexyl or benzyl esters.

Among the protective groups $R_1$ of the amino function, acyl groups of formula $R_3CO$— wherein $R_3$ can be hydrogen or a linear or branched $C_1$–$C_5$ alkyl or an optionally substituted aryl, such as for example formyl, acetyl or benzoyl, and carbamates of formula $R_4OCO$—, wherein $R_4$ can be a linear or branched $C_1$–$C_4$ alkyl or an optionally substituted aryl, such as for example methoxycarbonyl, tert-butoxycarbonyl or benzyloxycarbonyl, are preferred.

In the process object of the present invention preferred compounds of formula II are those wherein $R_2$ is hydrogen and $R_1$ is different from hydrogen, still more preferred are those wherein $R_2$ is hydrogen and $R_1$ is acetyl.

For a general reference to the use of the protective groups in organic chemistry, and more particularly, to the experimental conditions commonly used in the reaction for the protection and deprotection of the carboxy and amino groups, see Theodora W. Greene and Peter G. M. Wuts "Protective Groups in Organic Synthesis", John Wiley & Sons, Inc., II Ed., 1991.

The compounds of formula II, when $R_1$ is hydrogen, can be salified at the level of the amino group with mineral acids, preferably with hydrochloric acid.

The compounds of formula III represent dialkylcarbonates, such as for example, dimethyl or diethylcarbonate.

The dialkylcarbonates of formula III are known, commercially available compounds.

The compounds of formula III and II are preferably used in a molar ratio III:II from 0.5:1 to 4:1.

Still more preferably, the molar ratio of the compounds III:II is from 1.5:1 to 2.5:1.

The alkylation reaction is carried out in basic medium, in the presence of organic bases, such as alkyl or arylamines or aromatic compounds containing a basic nitrogen, or of inorganic bases such as hydroxides, hydrides or carbonates of alkali or alkaline-earth metals, or of organometallic derivatives, such as for example, alkali or alkaline-earth metals alkoxides.

Preferred examples of bases are sodium alkoxides of formula RONa wherein R has the above reported meanings.

Preferably, an alkoxide having the same residue R as the dialkylcarbonate of formula III to be used, for example sodium methoxide for a methylation with dimethylcarbonate, is selected.

The alkoxides of formula RONa can optionally be prepared in situ by reaction between metallic sodium and the corresponding alcohol ROH.

The molar ratio base:compound II changes depending on the number of groups which can be salified in the starting compound of formula H and it is preferably from 1:1 to 5:1, with respect to the starting compound.

Still more preferably, such a ratio is from 2:1 to 3:1.

Furthermore, the alkylation reaction is carried out in the presence of a suitable organic solvent, optionally in the presence of little amounts of water.

Examples of organic solvents are chlorinated solvents such as methylene chloride, chloroform or trichloroethane, ethers such as diethylether, tetrahydrofuran or dioxane, aromatic hydrocarbons such as benzene, toluene or xylenes, aliphatic, aromatic or heteroaromatic amines such as triethylamine or pyridine, esters such as ethylacetate, ketones such as acetone or methylethylketone, dipolar aprotic solvents such as dimethylacetamide, dimethylformamide, dimethylsulphoxide, acetonitrile or N-methylpyrrolidone, dialkylcarbonates such as dimethylcarbonate or diethylcarbonate, lower alcohols such as methanol, ethanol, n-propanol, isopropanol, n-butanol, sec-butanol, isobutanol or tert-butanol or mixtures thereof.

From a practical point of view the lower alcohols are preferred.

In particular, the alcohol having the same alkyl residue R as the dialkylcarbonate for the alkylation reaction is preferably used. For example, the methylation of a compound of formula II with dimethylcarbonate is preferably carried out in methanol.

The reaction temperature is generally between the room temperature and the reflux temperature of the reaction mixture.

Preferably, the reflux temperature is used.

The process object of the present invention is preferably carried out under inert atmosphere, in order to avoid the oxidation of the starting compounds of formula II to disulphides.

The compounds of formula I and II have a stereogenic centre.

The process object of the present invention can be carried out starting from L- or D-cysteines of formula II and allows to obtain S-alkylcysteines of formula I without a significant racemization of the chiral centre.

According to the process object of the present invention, the final compounds of formula I are prepared by alkylation reaction of the starting compounds of formula II and, when $R_1$ and $R_2$ are different from hydrogen, by subsequent removal of the protective groups.

The reactions for the removal of the protective groups are carried out by using procedures which ensure the preservation of the optical purity of the compound.

The process object of the present invention is preferably used for the preparation of S-methylcysteine or of S-ethylcysteine, still more preferably for the preparation of S-methyl-L-cysteine.

According to a practical preferred embodiment of the process object of the present invention, the compound of formula II wherein $R_1$ is acetyl and $R_2$ is hydrogen is added to the solution of sodium alkoxide and dialkylcarbonate in alcohol, kept under stirring, at room temperature and under inert atmosphere.

The reaction mixture is then heated under reflux for the time necessary to the completeness of the reaction, cooled to room temperature and suitably treated with mineral acids.

The compound of formula I in a protected form is obtained by extraction from the aqueous phase with a suitable organic solvent.

The subsequent deprotection reaction, carried out according to conventional techniques, leads to the final compounds of formula I.

The process object of the present invention is of easy applicability and allows to obtain the S-alkylcysteines of formula I under mild conditions and with good yields.

A remarkable advantage of the process object of the present invention consists in the use of dialkylcarbonates, which are harmless and easy to handle reagents, instead of the traditional alkylating agents such as alkyl iodides or sulfates which require, for the industrial use, particular cautions and expensive security procedures because of their high toxicity.

Furthermore, in the processes using alkyl iodides or alkyl sulfates, the final product is formed in admixture with remarkable amounts of the corresponding salts which, for their intrinsic solubility characteristics, make more difficult the procedures for the purification, as already underlined.

On the contrary, in the process object of the present invention the use of dialkylcarbonates as alkylating agents results in the development of carbonic anhydride as the sole by-product during the final work-up in acid medium: the salts which are formed in the reaction medium derive exclusively from the bases and from the acids used in the process and not from the decomposition of the alokylating agent.

Consequently, there is not only a significant decrease in the amount of salts but also the possibility of avoiding the presence of undesired salts by suitably selecting the acidifying medium so making easier the purification procedures, even if the reagent is used in an amount higher than the stoichiometric one.

Moreover, starting from a compound of formula II in the form of a single stereoisomer, the present process allows to obtain the compounds of formula I with a high optical purity, without the occurrence of a significant racemization.

In conclusion, the use of reagents which are stable, cheap, easy to handle, commercially available, harmless, easy decomposable with acids at the end of the reaction and easy to remove makes the process object of the present invention particularly suitable for the industrial application.

In order to illustrate the present invention the following examples are now given.

EXAMPLE 1

Preparation of S-methyl-L-cysteine from L-cysteine

Into a 2 l double-jacket reactor, equipped with mechanic stirrer, thermometer and reflux condenser, kept under nitrogen, methanol (700 g) and L-cysteine hydrochloride monohydrate (175.5 g, 1 mole) were added at room temperature.

The mixture was kept under stirring up to dissolution and then a 30% w/w solution of sodium methoxide in methanol (540 g, 3 moles) was added dropwise in 15 minutes, allowing the temperature to raise spontaneously. During the addition the precipitation of a solid occurred.

Dimethylcarbonate (180 g, 2 moles) was added to the resultant suspension and the mixture was then heated at the reflux temperature for 24 hours.

After cooling to 20–30° C., 32% w/w hydrochloric acid (230 g, 2 moles) was added dropwise, by controlling the development of carbonic anhydride and keeping the temperature below 40° C.

At the end of the addition, the reaction mass was brought to residue under vacuum, obtaining a crude product (320 g).

The resultant solid was taken up with glacial acetic acid (1300 g) and the resultant suspension was kept under stirring at the temperature of 90–100° C. for about 1 hour.

The present solid was removed by filtration at 90–100° C. and the filter was washed with glacial acetic acid (80 g) preheated at 90–100° C.

The filtered solution was concentrated under vacuum up to obtain a solid residue (290 g) which was added with methanol (1000 g).

The resultant suspension was kept under stirring for 2 hours at room temperature and then filtered. The solid was washed with methanol (2×150 g). A wet product (130 g) was obtained and dried under vacuum at 40° C. for 16 hours yielding dry S-methyl-L-cysteine (76 g).

$^1$H-NMR titre (internal standard dimethylsulphoxide): about 92%.

Molar yield (with respect to L-cysteine): about 52%.

The product can be purified from the presence of sodium chloride by repeating the treatment with acetic acid.

EXAMPLE 2

Preparation of N-acetyl-S-methyl-L-cysteine from N-acetyl-L-cysteine

Into a 1.5 l double-jacket reactor, equipped with mechanic stirrer, thermometer and reflux condenser, kept under nitrogen, a 30% w/w solution of sodium methoxide in methanol (360 g, 2 moles) and dimethylcarbonate (180 g, 2 moles) were charged at room temperature.

N-acetyl-L-cysteine (163 g, 1 mole) was added to the solution, under stirring and at room temperature, allowing the temperature to raise spontaneously during the addition. The resultant solution was heated for 1 hour at the reflux temperature and subsequently cooled to 25–30° C.

Water (500 g) was added in one portion to the reaction mixture and 32% w/w hydrochloric acid (230 g, 2 moles) was slowly added to the resultant solution, at such a speed to control the development of carbonic anhydride.

The solution was heated at about 50–60° C. and concentrated under vacuum up to a residual volume of about 650 ml.

The residual solution was cooled to 20–30° C. and extracted with ethyl acetate (500 g). The aqueous phase was extracted again with ethyl acetate (2×250 g).

The collected organic phases were concentrated under vacuum at the maximum temperature of 70° C., up to the obtainment of an oily residue (184 g) with a content of ethyl acetate lower than 5% by weight, usable as such in the subsequent step.

$^1$H-NMR titre: about 95% (internal standard dimethylsulphoxide).

Molar yield: about 98%.

Into a 1 l double-jacket reactor, kept under nitrogen, equipped with mechanical stirrer, thermometer, reflux condenser and dropping funnel, 48% w/w hydrobromic acid (338 g, 2 moles) was charged. Then the mixture was heated at 105±5° C. and, in about 3 hours, a solution of N-acetyl-S-methyl-L-cysteine (about 95% w/w, 184 g, 1 mole) in water (90 g), prepared by mixing the components and by heating under stirring at 60–70° C. up to complete dissolution, was added.

At the end of the addition the solution was kept at 105° C. for 1 hour.

The solution was cooled at 30–40° C. and a 30% w/w aqueous solution of sodium hydroxide (270 g, 2 moles) was added dropwise, keeping the temperature below 60–70° C.

L4S coal (2 g) and celite (6 g) were added to the resultant solution, keeping under stirring at 60–70° C. for 15 minutes.

The mixture was filtered and then the reactor and the filter were washed with water (20 ml). The resultant aqueous solution was concentrated under vacuum at the internal temperature of 60–70° C., up to the obtainment of a thick mass which can be stirred, with a residual volume of about 220 ml.

By keeping the mixture under stirring at the temperature of about 60° C. methanol (580 g) was added and a precipitate was formed. The mixture was cooled at 20° C. in 2 hours and, after further 2 hours, it was filtered.

The resultant solid was washed with methanol (2×40 g) obtaining a wet product (151 g) which, dried under vacuum at 40–50° C. for 16 hours, yielded dry S-methyl-L-cysteine (109 g).

$^1$H-NMR titre: 84% (internal standard dimethylsulphoxide).

Bromides (argentometric titre): 15%.

The solid was than suspended in methanol (300 g) and heated at the reflux temperature for 1 hour, under nitrogen.

The resultant mixture was cooled at 20° C. in 2 hours and, after further 2 hours at this temperature, was filtered.

The resultant solid was washed with methanol (2×15 g). The wet product (94 g) was dried for 16 hours under vacuum at 40–50° C., yielding pure S-methyl-L-cysteine (88 g).

$^1$H-NMR titre: 99% (internal standard dimethylsulphoxide).

Bromides (argentometric titre): 0.2%.

$[\alpha]^{20}_D = -29.7°$ (C=1, H$_2$O).

Molar yield (calculated starting from N-acetyl-L-cysteine): 64.5%.

We claim:

1. A process for the preparation of S-alkylcysteines of formula

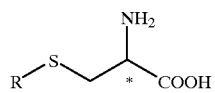

(I)

wherein

R is a linear or branched $C_1$–$C_4$ alkyl group;

the carbon atom marked by the asterisk is a stereogenic centre; comprising the treatment of a compound of formula

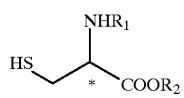

(II)

wherein $R_1$ is hydrogen or a linear or branched $C_1$–$C_6$ aliphatic acyl group, or an arylcarbonyl group, or an alkoxycarbonyl or aryloxycarbonyl group, wherein the alkyl moiety is a linear or branched $C_1$–$C_4$ alkyl, optionally substituted;

$R_2$ is a hydrogen atom or an optionally substituted linear or branched $C_1$–$C_6$ alkyl or an optionally substituted benzyl group;

wherein the carbon atom marked by the asterisk has the above reported meaning;

with a dialkylcarbonate of formula $$(RO)_2CO \qquad (III)$$

wherein

R has the above reported meanings;

in the presence of a suitable organic or inorganic base;

and the optional hydrolysis reaction, when one or both $R_1$ and $R_2$ are different from hydrogen.

2. A process according to claim 1 wherein the compound of formula III is dimethylcarbonate or diethylcarbonate.

3. A process according to claim 1 wherein the compounds of formula III and II are used in a molar ratio from 0.5:1 to 4:1.

4. A process according to claim 3 wherein the compounds of formula III and II are used in a molar ratio from 1.5:1 to 2.5:1.

5. A process according to claim 1 wherein the base and the compound of formula II are used in a molar ratio from 1:1 to 5:1.

6. A process according to claim 5 wherein the base and the compound of formula II are used in a molar ratio from 2:1 to 3:1.

7. A process according to claim 1 wherein the base is an alkoxide of formula RONa.

8. A process according to claim 7 wherein the base is sodium methoxide.

9. A process according to claim 1 wherein the solvent is a lower alcohol.

10. A process according to claim 9 wherein the solvent is methanol.

11. A process according to claim 1 comprising the reaction of a compound of formula II wherein $R_1$ is a linear or branched $C_1$–$C_6$ aliphatic acyl.

12. A process according to claim 11 comprising the reaction of a compound of formula II herein $R_1$ is acetyl.

13. A process for the preparation of S-methylcysteine which comprises the treatment of N-acetyl-cysteine with dimethylcarbonate, in the presence of a suitable organic or inorganic base and the subsequent hydrolysis reaction of the N-acetyl group.

* * * * *